| United States Patent [19] | [11] Patent Number: | 4,966,988 |
|---|---|---|
| Schinski et al. | [45] Date of Patent: | Oct. 30, 1990 |

[54] PROCESS FOR PREPARING ACETONITRILE 3-TRIFLUOROMETHYL BENZENE

[75] Inventors: William L. Schinski, San Rafael; Peter Denisevich, Jr., Fairfax, both of Calif.

[73] Assignee: Chevron Research Company, San Francisco, Calif.

[21] Appl. No.: 312,140

[22] Filed: Feb. 17, 1989

[51] Int. Cl.$^5$ ............................................. C07C 253/14
[52] U.S. Cl. .................................... 558/342; 570/124; 570/145; 570/197
[58] Field of Search ................ 558/342; 570/124, 145, 570/197

[56] References Cited

U.S. PATENT DOCUMENTS

| 2,121,330 | 10/1935 | Scherer et al. | 570/145 |
|---|---|---|---|
| 2,956,084 | 10/1960 | Eng et al. | 570/197 |
| 3,136,822 | 6/1964 | Frainier | 558/342 |
| 3,350,467 | 10/1967 | Larco et al. | 570/197 |
| 3,363,013 | 1/1968 | Kyker et al. | 570/197 |
| 3,966,832 | 6/1976 | Lademan et al. | 570/145 |
| 4,163,753 | 8/1979 | Pivawer | 558/342 |
| 4,252,624 | 2/1981 | Stephan | 558/342 |
| 4,328,374 | 5/1982 | Yoshinaka et al. | 558/342 |
| 4,360,478 | 11/1982 | Tieman | 558/342 |
| 4,467,125 | 8/1984 | Chupp et al. | 558/342 |
| 4,568,376 | 2/1986 | Ward | 558/342 |
| 4,593,144 | 6/1986 | Chupp et al. | 558/342 |

FOREIGN PATENT DOCUMENTS

| 0165322 | 12/1985 | European Pat. Off. | 558/342 |
|---|---|---|---|
| 1024656 | 3/1966 | United Kingdom | 558/342 |
| 20710871-A | 9/1981 | United Kingdom | 558/342 |

OTHER PUBLICATIONS

Chupp et al., *Synthesis,* 224–226 (Mar. 1986).

*Primary Examiner*—John M. Ford
*Assistant Examiner*—J. Richter
*Attorney, Agent, or Firm*—R. C. Gaffney; L. S. Squires

[57] ABSTRACT

A method is provided for forming (3-trifluoromethylphenyl)acetonitrile through the intermediate $\alpha,\alpha,\alpha$-trifluoro-$\alpha'$-chloro-m-xylene. This intermediate is formed by selective chlorination of $\alpha,\alpha,\alpha'$-trichloro-m-xylene under conditions which maximize yield and minimize the formation of undesired, non-recyclable chlorinated by-products.

20 Claims, No Drawings

PROCESS FOR PREPARING ACETONITRILE 3-TRIFLUOROMETHYL BENZENE

The present invention relates to a process for preparing 3-trifluoromethyl benzyl chloride. The present invention is also directed to a preparation of the important intermediate (3-trifluoromethylphenyl)acetonitrile via 3-trifluoromethyl benzyl chloride.

BACKGROUND OF THE INVENTION

The compound (3-trifluoromethyl-phenyl)acetonitrile is an important intermediate to agricultural and pharmaceutical chemicals and may be made directly from 3-trifluoromethyl benzyl chloride by treatment with sodium cyanide. For example, (3-trifluoromethylphenyl)acetonitrile is an intermediate for preparing herbicides disclosed in U.S. Pat. No. 4,568,376. However, to make large amounts of (3-trifluoromethylphenyl)acetonitrile in an economically advantageous manner, it is necessary to design a synthesis of 3-trifluoromethyl benzyl chloride which is economically feasible both in chemistry (e.g., selectivity and yields of the synthetic steps), use of reagents, and also in the apparatus utilized to conduct the processes.

It is thus an object of the present invention to provide a new process for preparing 3-trifluoromethyl benzyl chloride and (3-trifluoromethylphenyl)acetonitrile.

It is a further object of the present invention to provide an improved method for selectively monochlorinating 3-(chloromethyl) benzalchloride (sometimes referred to herein as CMBC or $\alpha,\alpha,\alpha'$-trichloro-m-xylene) to form 3-(chloromethyl) benzotrichloride (sometimes referred to herein as CMBTC), the latter of which is a key intermediate to forming trifluoromethyl benzyl chloride.

These and other objects of the present invention will be apparent from the following description, the appended drawing and appended claims, and from practice of the invention.

SUMMARY OF THE INVENTION

The present invention provides a new process for preparing (3-trifluoromethyl-phenyl)acetonitrile and its precursor, 3-trifluoromethyl benzyl chloride. The process generally involves chlorinating m-xylene under conditions to maximize the yield of $\alpha,\alpha,\alpha'$-trichloro-m-xylene (CMBC), while minimizing the formation of tetra-, penta- and hexachloro-m-xylenes. The CMBC is then selectively converted to CMBTC by chlorination with a chlorinating agent in strong basic conditions which maximize the formation of CMBTC, and minimize formation of undesired side products, such as ethers. The CMBTC is then converted to trifluoromethyl benzyl chloride by treatment with hydrogen fluoride. Subsequent treatment with sodium cyanide produces (3-trifluoromethyl-phenyl)acetonitrile.

A more thorough disclosure of the present invention and its preferred embodiments is presented in the detailed description which follows.

DESCRIPTION OF THE PREFERRED EMBODIMENTS

The present invention provides a novel and advantageous process for preparing (3-trifluoromethyl-phenyl)acetonitrile and its precursor, 3-trifluoromethyl benzyl chloride, according to the following steps.

The first step involves the chlorination of m-xylene by treatment with molecular chlorine under free-radical conditions catalyzed by ultraviolet radiation or chemical initiators. A scavenger such as pyridine, trialkyl- or triarylphosphates, or others known in the art may be added to suppress the formation of ring-chlorinated by-products. The reaction should be carried out under conditions whereby the xylene and lower (i.e., lower than trichlorinated) chlorinated by-products are the major by-products, rather than tetra-, penta- or hexachlorinated m-xylenes, which cannot be recycled. This can be attained by maintaining the temperature of m-xylene between about 100° C. to 130° C. at atmospheric pressure and slowly introducing chlorine gas under ultraviolet irradiation through the liquid. On startup or for batch processing, this is continued until approximately 3 moles of chlorine per mole of xylene have been absorbed: at this point the reaction mixture will contain about 35-45 mole per cent (preferably about 40 mole %) of the desired $\alpha,\alpha,\alpha'$-trichloro-m-xylene (CMBC). Upon completion of the reaction the mixture is distilled and the lighter fractions (less than trichlorinated) are recycled. During chlorination of these recycled lighter fractions which have been added to xylene, chlorine is added until about 1.9 moles of chlorine/mole xylene have been absorbed (again corresponding to formation of about 35-45 mole per cent (preferably about 40 mole %) of CMBC in the reaction mixture). The $\alpha,\alpha,\alpha'$-trichloro-m-xylene (CMBC) may be distilled and obtained in a purity of greater than 90%. In a particularly preferred embodiment of this step, the $\alpha,\alpha,\alpha'$-trichloro-m-xylene (CMBC) is not distilled but carried forward as a crude material (ca. 70% purity) to the next steps. The recycle of underchlorinated material (thus minimizing chlorine and xylene consumption and production of wastes) and the avoidance of elaborate distillation are particular advantages of this process.

In the second step in accordance with the present invention, the $\alpha,\alpha,\alpha'$-trichloro-m-xylene (CMBC), either in pure form as distilled from the reaction mixture of the first step or in crude form in the reaction mixture of the first step, is treated with a chlorinating agent, preferably hexachloroethane, in presence of a strong aqueous base to selectively monochlorinate CMBC to form CMBTC in about an 85%, or higher, yield. This is an unexpected advantage since not only is there high yield, but selectivity is also attained, while still achieving other desirable process features such as the elimination of foaming (which is prevalent in this type of reaction due to the formation of water as a by-product, which normally needs to be moved by azeotropic distillation during the reaction). The chlorination may be alternatively, but less preferably, conducted by use of carbon tetrachloride or a mixture of carbon tetrachloride and hexachloroethane as the chlorinating agent instead of hexachloroethane.

Preferred conditions for obtaining the selectivity and yields according to the present invention are to utilize a strong aqueous base, preferably sodium hydroxide or potassium hydroxide, in a concentrated aqueous solution, preferably greater than 50% and most preferably at least 75% sodium hydroxide (or potassium hydroxide), in sufficient amount to provide approximately 2 to 3 equivalents of base per equivalent of CMBC to be converted.

Furthermore, use of high concentrations of water in the aqueous solution, taken with the production of water as a by-product of the reaction, would normally require that the water be removed during the reaction by azeotropic distillation, a process usually requiring reflux conditions which causes undesirable foaming. But solid potassium hydroxide or sodium hydroxide are equally undesirable because the yields and selectivity achieved are not advantageous.

As set forth above, use of about two equivalents or less of hexachloroethane, the preferred chlorinating reagent, in high concentration in solution is particularly advantageous. Since hexachloroethane is a solid at normal temperatures, the formation of a solution using a minimum of solvent is preferred. An additional advantage is that, upon loss of two chlorine atoms, hexachloroethane is converted to tetrachloroethylene, which in turn can be recycled after re-chlorination with molecular chlorine. Some suitable inert solvents such as hexane, toluene, and the like, as well as compatible mixtures thereof, can be used, preferably in small amounts. The particularly preferred solvent is tetrachloroethylene, since it is a co-product of the reaction and can be readily recycled along with the hexachloroethane. Since the hexachloroethane and the chlorinated reactants and by-products are insoluble in water, the reaction will be conducted in two phases and therefore preferably a phase transfer catalyst should be utilized. The preferred catalysts are the long chain trialkyammonium halides, such as n-dodecyl-trimethylammonium halide. Alkyl ammonium salts, such as tetrabutylammonium salts, may also be utilized. The temperature of the reaction is preferably within the range of about 40° to 120° C. at atmospheric pressure. The reaction should preferably be conducted for about 3 to 6 hours. It has been found that the time-temperature profile of the reaction is important since, if the reaction is unduly prolonged, the yield of the desired CMBTC product begins to decrease.

In the following table there are shown the yields of the desired CMBTC product as measured by crude analysis by gas chromatography, and by actual yield by isolation of final product. The following table shows a variation of the equivalents of hydroxide from 1.2 equivalents to 4 equivalents, and the equivalents of hexachloroethane from 1.1 equivalents to 2 equivalents. The reaction was monitored for the initial hydroxide concentration in the aqueous phase to the final hydroxide concentration in the aqueous phase. The percent ROR shows the percent formed of the undesired ether product. Finally, the time of reaction is given. The first two entries of the table using 4 equivalents of hydroxide (50% by weight initial hydroxide concentration) entailed the azeotropic removal of water during the reaction. The concentration of the hydroxide at an initial concentration of 75% (by weight) in water and higher, eliminates the need for azeotropic distillation of water from the reaction. Therefore, the reaction need not be conducted under reflux and foaming is avoided. It was thus found that the use of about 2 equivalents of hexachloroethane and about 2 to 3 equivalents of hydroxide maximizes conversion of the desired product (attaining yields of about 85% or greater) without unnecessarily contaminating the reaction product with by-products.

TABLE

| eqs. OH$^-$ | eqs. HCE | [OH$^-$]$_i$ | [OH$^-$]$_f$ | GC | yield | % ROR | time |
|---|---|---|---|---|---|---|---|
| 4 | 1.1 | 50% | >90% | 53% | — | 27% | 3 hrs |
| 4 | 2 | 50% | >90% | 66% | — | 10% | — |
| 3 | 2 | 75% | 57% | 87% | 85% | 5% | 3.5 |
| 1.2 | 1.2 | 75% | — | 47% | — | 8% | 4.0 |
| 2 | 2 | 75% | 47% | 89% | 63% | 1.5% | 6.5 |
| 2 | 1.5 | 80% | 47% | 81% | 53% | 8% | 8.0 |
| 2 | 1.5 | 75% | 47% | 80% | 70% | 9% | 7.5 |
| 2.5 | 2 | 80% | 58% | 87% | 84% | 2.3% | 5.33 |

The CMBTC may be removed and purified from the reaction mixture by separating the organic phase from the reaction mixture, washing with water and distilling and recycling the excess hexachloroethane and co-product tetrachloroethylene. The $\alpha,\alpha,\alpha,\alpha'$-tetrachloro-m-xylene (CMBTC) may then be quickly distilled to remove non-volatile by-products such as ethers. If this second step is carried out with substantially pure $\alpha,\alpha,\alpha'$-trichloro-m-xylene (CMBC), the product CMBTC is of high purity. In the particularly preferred embodiment in which the CMBC is carried into the second step after only distilling out and recycling the lighter materials, the product CMBTC will contain ca. 15–30% $\alpha,\alpha,\alpha,\alpha',\alpha',\alpha'$-hexachloro-m-xylene (derived from tetra- and pentachloro-m-xylene impurities in the CMBC). This crude CMBTC may be distilled to greater than 90% purity but is preferably carried forward without additional purification to the third step.

The third step of the reaction involves fluorination of CMBTC with hydrogen fluoride, which selectively converts the trichloromethyl group to a trifluoromethyl group without fluorination, hydrolysis or other undesired side reaction at the chloromethyl group of CMBTC. Typical choices of reaction conditions include, but are not limited to:

1. Fluorination with liquid hydrogen fluoride at atmospheric pressure in the temperature range of about 0° to 15° C.
2. Fluorination with liquid hydrogen fluoride above atmospheric pressure, preferably in the temperature range of about 25° to 120° C.
3. Fluorination with gaseous hydrogen fluoride at or above atmospheric pressure, preferably in the temperature range of about 50° to 120° C.

In the above cases, catalysts known in the art for the conversion of benzotrichloride to benzotrifluoride, such as fluorides and chlorides of antimony, phosphorus, tantalum, niobium, etc. may be added to increase the rate and/or selectivity of the fluorination.

The desired product of this reaction is $\alpha,\alpha,\alpha$-trifluoro-$\alpha'$chloro-m-xylene. In the particularly preferred embodiment of the second step of the synthesis in which crude CMBTC was carried forward, the impurity, $\alpha,\alpha,\alpha,\alpha',\alpha',\alpha'$-hexachloro-m-xylene, is converted during the fluorination to the corresponding hexafluoro-m-xylene which is easily removed by distillation to give the product in a pure state.

A particular advantage of the present process is that the difficult fractional distillation of the high boiling trichloro-, tetra-, penta-, and hexachloroxylenes is avoided since undesired impurities are carried forward through the process and eventually converted to the low boiling and easily removed hexafluoro-m-xylene. The cost of the small increase in hydrogen fluoride consumption resulting from the presence of hexachloro-m-xylene is more than compensated by the resulting simplification of the process.

The fourth step according to the present invention involves the treatment of α,α,α'-trifluoro-α'-chloromxylene with an alkali metal cyanide to produce (3-trifluoromethyl-phenyl)acetonitrile. This may be accomplished by mixing the trifluorochloro-metaxylene with an alkali metal cyanide, preferably sodium cyanide in water in the presence of a phase-transfer catalyst, such as quaternary ammonium salt, preferably ALIQUAT® 336 (methyl tricapryl ammonium chloride) or ALIQUAT® 4 (dodecyl trimethyl ammonium chloride), or a crown ether. A co-solvent, preferably one which is miscible with water, such as methanol or another lower alcohol, acetonitrile, or the like, may be added. After a reaction time of about 6 to 9 hours, preferably around 8 hours at around 70° to 80° C., preferably 78° C., the mixture may be diluted with water and the organic phase may be separated, from which the (3-trifluoromethylphenyl)acetonitrile isolated, for example, by distillation. Yield for this step is typically about 90 to 92% with an assay of greater than 98% purity. The (3-trifluoromethyl-phenyl)acetonitrile is an important chemical intermediate and the 3-trifluoromethyl benzyl chloride is an important intermediate for preparing that chemical. In addition, the 3-trifluoromethyl benzyl chloride is an important intermediate for preparation of a variety of meta-difunctional benzenes.

The following examples are presented to illustrate, in general, the present invention, as well as some of the various embodiments of the invention. These examples are presented as being illustrative of the novel processes of the invention and are not intended to be limitations to the scope thereof.

EXAMPLE 1

Preparation of α,α,α'-trichloro-m-xylene m-Xylene (3226 grams, 30 moles) was charged to a 5-liter 3-neck flask, equipped with a reflux condenser and gas inlet (dispersion) tube. Pyridine (3.0 mls.) was added and the mixture heated to 125° C. The flask was continually irradiated with a commercial sunlamp (GE) and chlorine gas was passed through the 130° C. by regulating the chlorine flow. A total of 5298 grams (74.6 moles) of chlorine was added over 19 hours. The resulting mixture of chlorinated xylene had the composition:
α-chloroxylene 3.5%
α,α-dichloroxylene 4.6%
α,α'-dichloroxylene 38.8%
α,α,α'-trichloroxylene 36.6%
tetrachloroxylene 6.2%
others balance.
The mixture was fractionally distilled through a 20-tray Oldershaw column to give 1393 grams of α,α,α'-trichloroxylene which assayed at 92%. An additional 462 grams assaying 81.4% were taken separately. The lighter fractions were kept for recycle.

EXAMPLE 2

Preparation of α,α,α,α'-tetrachloroxylene

α,α,α'-Trichloro-m-xylene (22.5 grams, 93.2% a.i., 0.1 moles) was dissolved in 18 mls. of tetrachloroethylene. Hexachloroethane (59.2 grams, 0.25 moles), potassium hydroxide (12.8 grams, 87.7%, 0.2 moles), water (2.13 grams), and dodecyltrimethylammonium chloride (0.255 grams, 0.001 moles) were added. The mixture was heated at 75° C. for 2.5 hours with good stirring. The reaction was quenched with 30 mls. of water and 18 mls tetrachloroethylene. The organic phase was separated and washed with water. The excess solvent and hexachloroethane were distilled off to give an 85.2% yield of α,α,α,α'-tetrachloroxylene with a purity of 84%.

EXAMPLE 3

Preparation of α,α,α-Trifluoro-α'-chloro-m-xylene

Liquid hydrogen fluoride (200 grams, 10 moles) is charged into a one-liter Hastelloy B autoclave. α,α,α,α'-Tetrachloroxylene (84%, 290 grams, 1 mole) was slowly added while the mixture was stirred vigorously and maintained (cooling) at 0°–10° C. Hydrogen chloride gas was allowed to vent through a reflux condenser and the condensed hydrogen fluoride was returned to the autoclave. After the addition was complete (2 hours) the mixture was stirred an additional 1 hour until hydrogen chloride evolution ceased. The mixture was allowed to warm to room temperature and the excess hydrogen fluoride evaporated. The remaining organic phase was washed with water (500 mls) and 10% sodium hydroxide (500 mls). The product was distilled under reduced pressure to give the product (165 grams, 85% yield, assay 93%). Lighter fractions contained primarily hexafluoro-m-xylene and the pot residue contained some partially fluorinated materials.

EXAMPLE 4

Preparation of α,α,α-Trifluoromethylphenylacetonitrile

The product above from Example 3 (2.0 moles) was combined with water (520 ml), acetonitrile (1 liter), sodium cyanide (2.2 moles), and methyl tricaproyl ammonium chloride (Aliquat ™ 336) (0.04 mole). The mixture was stirred and heated at 78° C. for 8 hours. The acetonitrile was removed in vacuo at 40° C. The residue was diluted with an additional 520 mls of water and the organic phase separated and dried over MgSO$_4$. The crude product (338 grams) was distilled through a 10-tray Oldershaw column at 2 mm Hg. A forerun (78 grams) assaying 91% was taken, followed by a main cut of 273 grams which assayed 98.%. The pot residue amounted to 36 grams.

Although this invention has been described with respect to specific embodiments, the details thereof are not to be construed as limitations, and it will be apparent that various embodiments and modifications may be resorted to without departing from the spirit and the scope of the invention, and it is understood that such equivalent embodiments are intended to be included within the scope of the present invention.

We claim:
1. A process for preparing a compound of formula I:

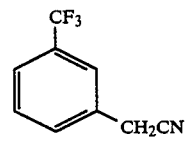

comprising the steps of:
A. chlorinating m-xylene to form a chlorinated mixture comprising α,α,α'-trichloro-m-xylene;
B. treating said α,α,α'-trichloro-m-xylene with a chlorinating agent selected from the group consisting of carbon tetrachloride, hexachloroethane and a combination thereof, in the presence of an aqueous solution containing greater than about 50% by weight of a hydroxide base and a phase transfer catalyst at a temperature in the range of about 40 to 120 degrees Centigrade at atmospheric pressure to form α,α,α,α'-tetrachloro-m-xylene;

C. treating said α,α,α,α'-tetrachloro-m-xylene with at least a stoichiometric amount of a fluorinating agent to form α,α,α-trifluoro-α'-chloro-m-xylene;

D. treating said α,α,α-trifluoro-α'-chloro-m-xylene with an alkali metal cyanide to form said compound of formula I.

2. A process according to claim 1 further comprising the step of distilling monochlorinated, dichlorinated and unchlorinated xylenes from said mixture formed in step A and recycling said xylenes.

3. A process for preparing a compound of the formula II:

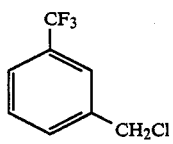

II comprising the steps of:
A. chlorinating m-xylene to form a chlorinated mixture comprising α,α,α'-trichloro-m-xylene;

B. treating said α,α,α'-trichloro-m-xylene with a chlorinating agent selected from the group consisting of carbon tetrachloride, hexachloroethane and a combination thereof, in the presence of an aqueous solution containing greater than about 50% by weight of a hydroxide base and a phase transfer catalyst at a temperature in the range of about 40 to 120 degrees Centigrade at atmospheric pressure to form α,α,α,α'-tetrachloro-m-xylene;

C. treating said α,α,α,α,'-tetrachloro-m-xylene with at least a stoichiometric amount of a fluorinating agent to form said compound of formula II.

4. A process according to claim 3 further comprising the step of distilling monochlorinated, dichlorinated and unchlorinated xylenes from said mixture formed in step A and recycling said xylenes.

5. A process according to claim 1 or 3 wherein said chlorinating agent in step B comprises hexachloroethane which is converted to tetrachloroethylene pursuant to said step B,
and said process further comprises the step of treating said tetrachloroethylene with chlorine to regenerate hexachloroethane and recycling same as the chlorinating agent in said step B.

6. A process according to claim 1 or 3 wherein said chlorinating agent in step B comprises hexachloroethane.

7. A process according to claim 1 or 3 wherein said chlorinating agent in step A comprises molecular chlorine.

8. A process according to claim 1 or 3 wherein said fluorinating agent in said step C comprises hydrogen fluoride.

9. A process according to claim 1 wherein said alkali metal cyanide salt in said step D comprises sodium cyanide.

10. A process according to claim 1 or 3 wherein said base in said step B is provided in greater than 50% concentration by weight in an aqueous solution.

11. A process according to claim 1 or 3 wherein said base in said step B is provided in an amount of 2 to 3 equivalents of base per equivalent of α,α,α'-trichloro-m-xylene.

12. A method according to claim 1 or 3 wherein said hexachloroethane in said step B is provided in an amount of about 2 equivalents of hexachloroethane per equivalent of α,α,α'-trichloro-m-xylene.

13. A method according to claim 1 or 3 wherein said step B is performed at a temperature within the range of 40° to 120° C.

14. A method according to claim 1 or 3 wherein said step B is conducted in the presence of a phase transfer catalyst.

15. A method according to claim 14 wherein said phase transfer catalyst comprises a tetraalkyl ammonium salt.

16. A process according to claim 15 wherein said tetraalkyl ammonium salt is selected from the group consisting of n-dodecyltrimethyl ammonium chloride and methyl tricapryl ammonium chloride.

17. A process according to claim 13 wherein said step B is conducted for a period of from about 3 to about 6 hours.

18. A process according to claim 1 or 3 wherein the liquid reaction mixture used in step B comprises an organic phase comprising hexachloroethane, in which the products of said step are soluble.

19. A process according to claim 7 wherein a sufficient amount of molecular chlorine is used so that chlorination is completed when said mixture comprises about 35–45 mole per cent α,α,α'-trichloro-m-xylene.

20. A process according to claim 19 wherein chlorination is completed when said mixture comprises about 40 mole per cent α,α,α'-trichloro-m-xylene.

* * * * *